(12) United States Patent
Kanazirev et al.

(10) Patent No.: US 8,314,277 B2
(45) Date of Patent: Nov. 20, 2012

(54) ADSORBENT FOR FEED AND PRODUCTS PURIFICATION IN BENZENE SATURATION PROCESS

(75) Inventors: Vladislav I. Kanazirev, Arlington Heights, IL (US); Jayant K. Gorawara, Buffalo Grove, IL (US); Dana K. Sullivan, Mount Prospect, IL (US); Richard R. Rosin, Glencoe, IL (US)

(73) Assignee: UOP LLC, Des Plaines, IL (US)

( * ) Notice: Subject to any disclaimer, the term of this patent is extended or adjusted under 35 U.S.C. 154(b) by 33 days.

(21) Appl. No.: 13/151,449

(22) Filed: Jun. 2, 2011

(65) Prior Publication Data

US 2012/0004480 A1 Jan. 5, 2012

Related U.S. Application Data

(60) Provisional application No. 61/359,908, filed on Jun. 30, 2010.

(51) Int. Cl.
*C07C 5/10* (2006.01)
(52) U.S. Cl. .......................... 585/266; 585/267; 585/270
(58) Field of Classification Search .................. 585/266, 585/267, 270
See application file for complete search history.

(56) References Cited

U.S. PATENT DOCUMENTS

| | | | |
|---|---|---|---|
| 2,915,365 A | 12/1959 | Saussol |
| 4,028,223 A | 6/1977 | Hayes et al. |
| 4,087,383 A | 5/1978 | Gernand et al. |
| 4,155,835 A | 5/1979 | Antal |
| 4,592,829 A | 6/1986 | Eberly, Jr. |
| 4,695,366 A | 9/1987 | Miller et al. |
| 4,863,894 A | 9/1989 | Chinchen et al. |
| 5,003,118 A | 3/1991 | Low et al. |
| 5,227,351 A | 7/1993 | Gasper-Galvin et al. |
| 5,663,466 A | 9/1997 | Rice et al. |
| 6,033,461 A | 3/2000 | Yang et al. |
| 6,224,840 B1 | 5/2001 | Kim et al. |
| 6,960,700 B1 | 11/2005 | Sethna et al. |
| 7,102,038 B2 | 9/2006 | Murray et al. |
| 7,291,259 B2 | 11/2007 | Gupta et al. |
| 7,618,558 B2 | 11/2009 | Nielsen |
| 7,906,088 B2 | 3/2011 | Kanazirev et al. |
| 2006/0261011 A1 | 11/2006 | Kanazirev et al. |
| 2008/0041227 A1 | 2/2008 | Mulvaney, III et al. |
| 2008/0119358 A1 | 5/2008 | Kanazirev et al. |
| 2008/0173586 A1 | 7/2008 | Kanazirev et al. |
| 2008/0271602 A1 | 11/2008 | Tatarchuk et al. |
| 2008/0286173 A1 | 11/2008 | Shecterle |
| 2008/0287724 A1 | 11/2008 | Shecterle |
| 2008/0289496 A1 | 11/2008 | Poshusta et al. |
| 2009/0155148 A1 | 6/2009 | Kanazirev |
| 2009/0266232 A1 | 10/2009 | Nakamura et al. |
| 2010/0326886 A1 | 12/2010 | Kanazirev et al. |
| 2012/0000825 A1 | 1/2012 | Kanazirev et al. |

FOREIGN PATENT DOCUMENTS

| | | |
|---|---|---|
| EP | 0865814 A2 | 9/1998 |
| JP | 10235185 A | 9/1998 |

OTHER PUBLICATIONS

Quinn, "Removal of Arsine from Synthesis Gas Using a Copper on Carbon Adsorbent", Ind. Eng. Chem. Res. 2006, 45, 6272-6278.
U.S. Appl. No. 13/218,031, filed Aug. 25, 2011, Vladislav I. Kanazirev et al.
Brazlauskas, "Synthesis and Properties of CuO/Zeolite Sandwich Type Adsorbent-Catalysts", Chin J Catal, 2008, 29(1): 25-30.
Buelna, "Preparation of spherical alumina and copper oxide coated alumina sorbents by improved sol-gel granulation process", Microporous and Mesoporous Materials 42 (2001) 67-76.
Iretskaya, "Promoting Effect of Chloride on the SO2 Adsorption Capacity and Adsorption Rate of Alumina-Supported Copper Oxide Adsorbents: Thermogravimetric and Infrared Studies", J. Phys. Chem. B 2003, 107, 4955-4962.
Li, "Metal Loaded Zeolite Adsorbents for Phosphine Removal", Ind. Eng. Chem. Res. 2008, 47, 1501-1505.
Wang, "Sol-Gel-Derived Alumina-Supported Copper Oxide Sorbent for Flue Gas Desulfurization", Ind. Eng. Chem. Res. 1998, 37, 4675-4681.

*Primary Examiner* — Thuan D Dang
(74) *Attorney, Agent, or Firm* — Mark Goldberg

(57) ABSTRACT

The service life and deactivation rate of a benzene saturation catalyst is improved through use of a new sulfur guard bed containing a chloride additive. This sulfur guard bed, which contains supported CuO material having an increased resistance to reduction, shows such improvement. Thus, the danger of run-away reduction followed by a massive release of water and deactivation of an isomerization catalyst is practically eliminated. The fact that the guard bed material preserves the active metal phase-copper in an active (oxide) form is an important advantage leading to very low sulfur content in the product stream. The sulfur capacity per unit weight of sorbent is also significantly increased, making this sorbent a superior cost effective sulfur guard product. The guard bed is effective in treating mixed phase feed streams.

13 Claims, No Drawings

ADSORBENT FOR FEED AND PRODUCTS PURIFICATION IN BENZENE SATURATION PROCESS

CROSS-REFERENCE TO RELATED APPLICATION

This application claims priority from Provisional Application No. 61/359,908 filed Jun. 30, 2010, the contents of which are hereby incorporated by reference.

BACKGROUND OF THE INVENTION

The present invention involves an improvement to the feed and product in a benzene saturation process. In particular the present invention provides an adsorbent that is effective for trace sulfur removal for feeds that comprise a mixture of phases to benzene saturation units as well as product streams to such units.

For most refiners, the issue of benzene in the gasoline pool is one of managing benzene production from the catalytic reformer. The two primary strategies to accomplish this goal include the minimization of benzene and benzene precursors in the catalytic reformer feed, or the elimination of the benzene from the reformate after it is formed. A benzene saturation unit can be applied in either of these strategies. For example, a benzene saturation unit can be located on the overhead stream of a naphtha splitter, to remove the natural benzene concentrated by aggressive reformer feed prefractionation. Alternatively, a benzene saturation unit can be used on a light reformate stream to remove the benzene that has been produced in the reformer.

The benzene saturation process was developed as a low-cost, stand-alone option to treat $C_5$-$C_6$ feedstocks that are high in benzene. Benzene is saturated with hydrogen to make $C_6$ naphthenes. The catalyst used in this process is highly selective for benzene saturation to $C_6$ naphthenes. Makeup hydrogen is provided in an amount slightly above the stoichiometric level required for benzene saturation. The heat of reaction associated with benzene saturation is carefully managed to control the temperature rise across the reactor. Use of a relatively high space velocity in the reactor contributes to the unit's cost-effectiveness. A benzene saturation unit can be located on a light reformate or light straight-run naphtha stream.

The operation of a benzene saturation unit is very sensitive to the presence of sulfur-containing compounds. The specification and catalyst sensitivity requires extremely low levels of sulfur with preferably less than 50 parts per billion weight of sulfur. It has been found that copper oxides are more effective than other oxides such as zinc oxide and nickel oxide in removing sulfur. Prior art copper oxides had the disadvantage of being reduced to copper metal during operation. This not only decreased their effectiveness in removing sulfur compounds, but since the reduction process is highly exothermic, when used in connection with gases that have a low specific heat, the temperature exotherm can result in unsafe conditions, especially on start-up.

In a prior art design for a benzene saturation unit there has been a separate sulfur guard bed on the naphtha feed, and if warranted by the sulfur content, a second one on the makeup hydrogen stream as well. Separate guard beds have been required due to previous sulfur adsorbents needing to operate in single phase, either vapor or liquid, to achieve the required outlet sulfur level. If a sulfur adsorbent could achieve the required degree of sulfur removal in a mixed phase stream comprising vapor and liquid, it would be possible to instead have a compound bed, with the sulfur adsorbent on top, and the Pt on alumina benzene saturation catalyst below it. This would save capital cost as no separate sulfur guard beds or the related heat exchangers would be needed.

Guard beds with supported copper oxide (CuO) are often used for feed purification in benzene saturation units. Unfortunately, the CuO reduces to a lower valence state, at the typical operating temperatures in the range of ambient temperature for a make-up hydrogen treater and 120° to 150° C. for liquids being treated. Typically in prior art systems, the reduction of CuO occurs rapidly, and large amounts of water are produced. The excessive moisture is disadvantageous to the operation of the benzene saturation catalyst. In addition, there is the undesired exotherm.

Copper containing materials are widely used in industry as catalysts and sorbents. The water shift reaction in which carbon monoxide is reacted in presence of steam to make carbon dioxide and hydrogen as well as the synthesis of methanol and higher alcohols are among the most practiced catalytic processes nowadays. Both processes employ copper oxide based mixed oxide catalysts.

Copper-containing sorbents play a major role in the removal of contaminants, such as sulfur compounds and metal hydrides, from gas and liquid streams. One new use for such sorbents involve the on-board reforming of gasoline to produce hydrogen for polymer electrolyte fuel cells (PEFC). The hydrogen feed to a PEFC must be purified to less than 50 parts per billion parts volume of hydrogen sulfide due to the deleterious effects to the fuel cell of exposure to sulfur compounds.

Copper oxide (CuO) normally is subject to reduction reactions upon being heated but it also can be reduced even at ambient temperatures in ultraviolet light or in the presence of photochemically generated atomic hydrogen.

The use of CuO on a support that can be reduced at relatively low temperatures is considered to be an asset for some applications where it is important to preserve high dispersion of the copper metal. According to U.S. Pat. No. 4,863,894, highly dispersed copper metal particles are produced when co-precipitated copper-zinc-aluminum basic carbonates are reduced with molecular hydrogen without preliminary heating of the carbonates to temperatures above 200° C. to produce the mixed oxides. However, easily reducible CuO is disadvantageous in some important applications, such as the removal of hydrogen sulfide from gas and liquid streams when very low residual concentration of $H_2S$ in the product is required The residual $H_2S$ concentration in the product gas is much higher by the laws of thermodynamics (which is undesirable) when the CuO reduces to Cu metal. in the course of the process since reaction (1) is less favored than the CuO sulfidation to CuS.

$$2Cu+H_2S=Cu_2S+H_2 \qquad (1)$$

The known approaches to reduce the reducibility of the supported CuO materials are based on combinations with other metal oxides such as $Cr_2O_3$. The disadvantages of the approach of using several metal oxides are that it complicates the manufacturing of the sorbent because of the need of additional components, production steps and high temperature to prepare the mixed oxides phase. As a result, the surface area and dispersion of the active component strongly diminish, which leads to performance loss. Moreover, the admixed oxides are more expensive than the basic CuO component which leads to an increase in the sorbent's overall production cost.

The present invention comprises a new method to improve feed purification in a benzene saturation process by using a supported CuO adsorbent which contains chloride as a means to decrease the tendency of CuO to be reduced to low valent state, especially Cu metal. Surprisingly, it has now been found that introducing chloride either in the basic copper carbonate, which serves as CuO precursor, or into the intermediate CuO-alumina adsorbent leads to material having improved resistance to reduction by under high pressure hydrogen. This feature is especially useful in the benzene saturation process. In addition, it has been found that the adsorbent used in the present invention can remove sulfur impurities from mixed vapor/liquid operation to the levels necessary to protect the benzene saturation catalyst.

SUMMARY OF THE INVENTION

The present invention provides an improved benzene saturation process that consists of using a sulfur removal guard bed that contains supported CuO material having an increased resistance to reduction. As a result of the use of this guard bed, the deactivation rate and the service life of the benzene saturation catalyst significantly improves. This invention employs a supported CuO material whereby the resistance of the CuO phase towards reduction has been significantly increased. Thus, the danger of run-away reduction followed by a massive release of water and deactivation of a benzene saturation catalyst is strongly diminished. Another important benefit is that the guard bed material preserves the active metal phase-copper in an active (oxide) form which is needed for complete sulfur removal. This advantage will result in a significant increase in sulfur capacity per unit weight of sorbent making this sorbent a more cost effective sulfur guard product. Another, important advantage is that the exothermic reaction of reduction of CuO to copper metal is avoided and even under strong reducing conditions, the material of the present invention will reduce mainly to cuprous oxide instead of to copper metal which is the case with prior art copper based sulfur adsorbents. In addition, the sulfur removal guard bed is effective in treating mixed phases of vapor and liquid.

The improved sulfur guard adsorbents of the present invention contain CuO supported on alumina wherein small amounts of an inorganic halide, such as sodium chloride is added to the carbonate precursor of CuO or to the intermediate adsorbent before the final thermal treatment (calcination) for a sufficient time at a temperature in the range 280° to 500° C. These reduction resistant sorbents show significant benefits in the removal of sulfur and other contaminants from gas and liquid streams. These sorbents are particularly useful in applications where the sorbents are not regenerated. Sulfur contaminants that are removed include hydrogen sulfide, light mercaptans, sulfides, disulfides, thiophenes and other organic sulfides and COS. Mercury can also be removed.

DETAILED DESCRIPTION OF THE INVENTION

Guard beds with supported copper oxide (CuO) are often used for feed purification in benzene saturation units. Unfortunately, the CuO reduces in the presence of the hydrogen, at the typical operating temperatures, which causes conversion of CuO to $Cu_2O$ and even to Cu metal, thereby producing water as reaction product. Typically the reduction of CuO occurs rapidly, and large amounts of water are produced. The excessive moisture could even overcome the down stream feed dryers and water leakage from the driers will cause irreversible catalyst deactivation. In addition, there are safety issues due to the high exotherm during the reduction of CuO and the presence of hydrogen.

Recent concerns about volatility and toxicity of hydrocarbon fuel and the resultant environment damage has prompted legislation that limits the content and composition of aromatic hydrocarbons in such fuels. Many of these limitations relate specifically to benzene which, due to its toxicity, is substantially eliminated from the gasoline pool. These fuels are generally referred to as reformulated gasolines. Requirements for reformulated gasoline have had profound impacts on the operation of refinery processes for producing high octane fuels. Reformulated gasoline requirements impose limitations on gasoline end points, benzene as well as total aromatics, and Reid vapor pressure (RVP).

Benzene reduction disrupts the previous operation methods of several hydrocarbon processes that produce high octane fuel. Benzene reduction poses some of the most severe problems for the operation of catalytic reformers that have been relied on to raise the octane of unleaded fuels. Reformers that were typically operated at high severity to produce high octane benzene and aromatic hydrocarbons must now be operated to eliminate benzene and reduce aromatics. Elimination of benzene can be accomplished by removing benzene or benzene precursors from hydrocarbons prior to hydrocarbon conversion processes or removing benzene from the product stream by saturation, separation or conversion. Methods for eliminating benzene from a reforming effluent include direct saturation or saturation through isomerization. It is well known to eliminate benzene by direct saturation of product or feed streams such as an isomerization zone feed. U.S. Pat. No. 5,003,118 teaches a process for the directly saturating benzene in a benzene saturation reactor and passing the remainder of the stream as feed to an isomerization zone. The benzene contribution from the reformate portion of the gasoline pool can also be decreased or eliminated by altering the operation of the reforming section. There are a variety of ways in which the operation of the refining section may be altered to reduce the reformate benzene concentration. Changing the cut point of the naphtha feed split between the reforming and isomerization zones from 82° to 93° C. (180° to 200° F.) will remove benzene, cyclohexane and methylcyclopentane from the reformer feed. Benzene can alternately also be removed from the reformate product by splitting the reformate into a heavy fraction and a light fraction that contains the majority of the benzene. Practicing either method will put a large quantity of benzene into the feed to other processing units, particularly the isomerization zone. Therefore, it is still necessary to have an efficient and cost effective means for removing benzene from feeds.

Suitable feedstocks for this invention will generally include $C_4+$ hydrocarbons up to an end boiling point of about 250° C. (482° F.). The feedstocks that are used in this invention will typically include hydrocarbon fractions rich in $C_5$-$C_7$ hydrocarbons. The term "rich" is defined to mean a stream having more than 50% of the mentioned component. In addition, the feedstock will include significant amounts of benzene. In order to realize the advantages of this invention, the concentration of benzene in the feedstock will usually at least equal 5 mol-% and will normally be higher. Preferably, in order to obtain the benefits of this invention, the concentration of benzene will equal at least 10 mol-% and more preferably at least 15 mol-%. Accordingly, the benzene content of the feed will normally be in a range of from 10 to 25 mol-%. There is no upper limit on the concentration of benzene. Where the saturation process of the invention is used in combination with an isomerization process, the maximum benzene content is dictated by the need to have sufficient paraffinic hydrocarbons present for the isomerization reaction. Other feed components will usually comprise $C_5$-$C_6$ cyclic and paraffinic hydrocarbons with normal and isohexane providing most of the paraffinic components.

The benzene saturation zone contacts the feed with a hydrogenation catalyst. The saturation zone will typically comprise a fixed bed of catalyst for promoting the hydrogenation of benzene. Suitable hydrogenation catalysts will provide a metallic function to promote hydrogen transfer without any substantial acid function that would lead to undesirable cracking Preferred catalyst compositions will include platinum group, tin or cobalt and molybdenum metals on suitable refractory inorganic oxide supports such as alumina. The alumina is preferably an anhydrous gamma-alumina with a high degree of purity. The term "platinum group metals" refers to noble metals excluding silver and gold which are selected from the group consisting of platinum, palladium, germanium, ruthenium, rhodium, osmium, and iridium.

Such catalysts will provide satisfactory benzene saturation at the operating conditions of this invention. The operating conditions include temperatures of from 249° to 316° C. (480° to 600° F.), preferably from 260° to 288° C. (500° to 550° F.), pressures of from 2068 to 4826 kPa (300 to 700 psig), preferably from 2758 to 3447 kPa (400 to 500 psig), and a 1 to 20 liquid hourly space velocity (LHSV), preferably from 4 to 12.

A particularly preferred catalyst comprises a platinum metal on an alumina support. In its preferred form the alumina support will comprise spheres having a nominal diameter of about 2 mm ($\frac{1}{16}$ inch) and surface area of from about 160 to 200 $m^2/g$ with an apparent bulk density of from about 0.45 to 0.6. Platinum metal may be present on the catalyst in a concentration of from 0.1 to 1 wt-% and preferably in a concentration of from 0.375 to 0.75 wt-%.

The hydrogenation zone catalyst and, when present, the isomerization zone catalyst are often sulfur sensitive. Suitable guard beds or adsorptive separation processes may be used to reduce the sulfur concentration of the feedstock. Preferably the sulfur in the feed to the saturation zone will have a sulfur concentration of less than 0.1 ppm. The sulfur concentration to most isomerization zones should be reduced to less than 0.5 ppm. The present invention provides an improved adsorbent for this purpose.

This invention employs a supported CuO material whereby the resistance of the CuO phase towards reduction has been significantly increased. Thus, the danger of run-away reduction followed by a massive release of water, deactivation of catalyst and dangerous exotherms is strongly diminished. In addition, the maximum water load to the down stream dryers is decreased. Finally, another important benefit is that the guard bed material preserves the active metal phase-copper in an active (oxide) form which is needed for complete sulfur removal. This advantage will result in a significant increase in sulfur capacity per unit weight of sorbent making this sorbent a more cost effective sulfur guard product. Since most of the CuO remains in its cupric form, the capacity of the adsorbent is greatly increased, up to being doubled when compared to a reduced copper product.

Basic copper carbonates such as $CuCO_3 \cdot Cu(OH)_2$ can be produced by precipitation of copper salts, such as $Cu(NO)_3$, $CuSO_4$ and $CuCl_2$, with sodium carbonate. Depending on the conditions used, and especially on washing the resulting precipitate, the final material may contain some residual product from the precipitation process. In the case of the $CuCl_2$ raw material, sodium chloride is a side product of the precipitation process. It has been determined that a commercially available basic copper carbonate that had both residual chloride and sodium, exhibited lower stability towards heating and improved resistance towards reduction than another commercial BCC that was practically chloride-free.

In some embodiments of the present invention, agglomerates are formed comprising a support material such as alumina, copper oxide from a precursor such as basic copper carbonate (BCC) and halide salts. The alumina is typically present in the form of transition alumina which comprises a mixture of poorly crystalline alumina phases such as "rho", "chi" and "pseudo gamma" aluminas which are capable of quick rehydration and can retain substantial amount of water in a reactive form. An aluminum hydroxide $Al(OH)_3$, such as Gibbsite, is a source for preparation of transition alumina. The typical industrial process for production of transition alumina includes milling Gibbsite to 1 to 20 microns particle size followed by flash calcination for a short contact time as described in the patent literature such as in U.S. Pat. No. 2,915,365. Amorphous aluminum hydroxide and other naturally found mineral crystalline hydroxides e.g., Bayerite and Nordstrandite or monoxide hydroxides (AlOOH) such as Boehmite and Diaspore can be also used as a source of transition alumina. In the experiments done in reduction to practice of the present invention, the transition alumina was supplied by the UOP LLC plant in Baton Rouge, La. The BET surface area of this transition alumina material is about 300 $m^2/g$ and the average pore diameter is about 30 Angstroms as determined by nitrogen adsorption.

Typically a solid oxysalt of a transitional metal is used as a component of the composite material. For the purpose of the examples presented of the present invention, we used basic copper carbonate (BCC), $CuCO_3Cu(OH)_2$ which is a synthetic form of the mineral malachite, produced by Phibro Tech, Ridgefield Park, N.J. The particle size of the BCC particles is approximately in the range of that of the transition alumina—1 to 20 microns. Another useful oxysalt would be Azurite—$Cu_3(CO_3)_2(OH)_2$. Generally, oxysalts of copper, nickel, iron, manganese, cobalt, zinc or a mixture of elements can be successfully used where copper is the main component.

The preferred inorganic halides are sodium chloride, potassium chloride or mixtures thereof. Bromide salts are also effective. The chloride content in the copper oxide sorbent may range from 0.05 to 2.5 mass-% and preferably is from 0.3 to 1.2 mass-%. Various forms of basic copper carbonate may be used with a preferred form being synthetic malachite, $CuCO_3Cu(OH)_2$.

The copper oxide sorbent that contains the halide salt exhibits a higher resistance to reduction by hydrocarbons and hydrogen than does a similar sorbent that is made without the halide salt. This feature is useful for feed purification in a benzene saturation process, especially for the removal of sulfur compounds In addition, the sorbent is useful in applications where the adsorbent is not regenerated. The removal of $H_2S$, light mercaptans, sulfides, disulfides, thiophenes and other organic sulfur compounds and carbonyl sulfide (COS) is an advantageous use of the adsorbent. Mercury can also be removed by this adsorbent.

Table 1 lists characteristic composition data of three different basic copper carbonate powder samples designated as Samples 1, 2 and 3.

TABLE 1

| Composition, Mass-% | Sample Number | | |
|---|---|---|---|
| | 1 | 2 | 3 |
| Copper | 55.9 | 55.4 | 54.2 |
| Carbon | 5.0 | 5.1 | 5.1 |
| Hydrogen | 1.3 | 1.2 | 1.2 |
| Sodium | 0.23 | 0.51 | 0.51 |
| Chloride | 0.01 | 0.32 | 0.28 |
| Sulfate | 0.06 | 0.01 | 0.02 |

All three samples were subjected to thermal treatment in nitrogen in a microbalance followed by reduction in a 5% $H_2$-95% $N_2$ stream. As the thermogravimetric (TG) analysis showed, chloride-containing BCC Samples 2 and 3 decompose to CuO at about 40° to 50° C. lower temperatures than Sample 1. On the other hand, the latter sample was found to reduce more easily in presence of $H_2$ than the Cl-containing samples. The reduction process completed with Sample 1 at 80° to 90° C. lower temperature than in the case of the Cl-containing Samples 2 and 3.

This reduction behavior was confirmed by preparing a mechanical mixture of NaCl and the Cl-free Sample 1 and then subjecting the mixture to a TG decomposition reduction test. In particular, 25 mg of NaCl reagent was intimately mixed with about 980 mg BCC (Sample 1). The mixture was homogenized for about 2 minutes using an agate mortar and pestle prior to TG measurements.

It was found that the addition of NaCl makes Sample 1 decompose more easily but also makes it resist reduction to a higher extent than in the case where no chloride is present. The observed effect of NaCl addition is definitely beyond the range of experimental error.

The exact mechanism of the chloride action is unknown at this point. We hypothesize that the salt additive may incorporate in some extent in the structure of the source BCC weakening it and making it more susceptible to decomposition. On the other hand, the copper oxide produced upon thermal decomposition of BCC now contains an extraneous species that may affect key elements of the metal oxide reduction process such as $H_2$ adsorption and activation and penetration of the reduction front throughout the CuO particle as well. We do not wish to favor any particular theory of Cl action at this point.

The series of experiments in which NaCl was added was conducted in a Perkin Elmer TGA-1 microbalance operated in a helium flow. The sample size was typically 8-10 mg. Both decomposition and reduction runs were conducted with one sample at a heating rate of about 25° C./min followed by short hold at 400° C. After cooling to about ambient temperature, 1.5% $H_2$-balance He—$N_2$ mixture was used as a reduction agent.

Table 2 presents data on several samples produced by mixing different amounts of NaCl or KCl powder to the BCC Sample 1 listed in Table 1.

TABLE 2

| Sample | Basic Cu carbonate, (g) | NaCl (g) | KCl (g) | Pre-treatment temperature, ° C. | Characteristic temperature, ° C. | |
|---|---|---|---|---|---|---|
| | | | | | BCC decomposition* | CuO reduction** |
| 1 | #1 only | 0 | 0 | 400 | 335 | 256 |
| 2 | 9.908 | 0.103 | 0 | 400 | 296 | 352 |
| 3 | 9.797 | 0.201 | 0 | 400 | 285 | 368 |
| 4 | 9.809 | 0.318 | 0 | 400 | 278 | 369 |
| 5 | 9.939 | 0 | 0.150 | 400 | 282 | 346 |
| 6 | 9.878 | 0 | 0.257 | 400 | 279 | 378 |
| 7 | 0.981 | 0 | 0.400 | 400 | 279 | 382 |
| 8 | #1 only | 0 | 0 | 500 | 333 | 310 |
| 9 | 9.797 | 0.201 | 0 | 500 | 282 | 386 |

*Temperature at which 20 mass-% sample weight is lost due to BCC decomposition
**Temperature at which 5% sample weight is lost due to CuO reduction The data also shows that both NaCl and KCl are effective as a source of Cl. Adding up to 1% Cl by weight affects strongly both decomposition temperature of BCC and the reduction temperature of the resulting CuO. It can be also seen that the combination of a thermal treatment at a temperature which is higher than the temperature needed for complete BCC decomposition and Cl addition leads to the most pronounced effect on CuO resistance towards reduction—compare Samples 3, 8 and 9 in Table 2.

Finally, the materials produced by conodulizing the CuO precursor—BCC with alumina followed by curing and activation retain the property of the basic Cu carbonate used as a feed. The BCC that is more resistant to reduction yielded a CuO-alumina sorbent which was difficult to reduce.

The following example illustrates one particular way of practicing this invention with respect of CuO-alumina composites: About 45 mass-% basic copper carbonate (BCC) and about 55 mass-% transition alumina (TA) produced by flash calcination were used to obtain 7×14 mesh beads by rotating the powder mixture in a commercial pan nodulizer while spraying with water. About 1000 g of the green beads were then additionally sprayed with about 40 cc 10% NaCl solution in a laboratory rotating pan followed by activation at about 400° C. The sample was then subjected to thermal treatment & reduction in the Perkin Elmer TGA apparatus as described earlier. Table 3 summarizes the results to show the increased resistance towards reduction of the NaCl sprayed sample.

TABLE 3

| Sample | Preparation condition | Characteristic temperature of TGA analysis, ° C. | |
|---|---|---|---|
| | | BCC decomposition* | CuO reduction** |
| 10 | Nontreated | 341 | 293 |
| 11 | Nontreated + activation | n/a | 302 |
| 12 | NaCl treated | 328 | 341 |
| 13 | NaCl treated + activation | n/a | 352 |

*Temperature at which 20 mass-% sample weight is lost due to BCC decomposition
**Temperature at which 5% sample weight is lost due to CuO reduction A cost-effective way to practice the invention is to leave more NaCl impurity in the basic Cu carbonate during the production. This can be done, for example, by modifying the procedure for the washing of the precipitated product. One can then use this modified BCC precursor to produce the sorbents according to our invention.

Another way to practice the invention is to mix solid chloride and metal oxide precursor (carbonate in this case) and to subject the mixture to calcinations to achieve conversion to oxide. Prior to the calcinations, the mixture can be co-formed with a carrier such as porous alumina. The formation process can be done by extrusion, pressing pellets or nodulizing in a pan or drum nodulizer.

Still another promising way to practice the invention is to co-nodulize metal oxide precursor and alumina by using a NaCl solution as a nodulizing liquid. The final product containing reduction resistant metal (copper) oxide would then be produced after proper curing and thermal activation.

The following Examples show the advantage of the present invention with regards to benzene saturation reactions.

Example 1

This example shows that according to the thermodynamics the achievement of a very low residual level of $H_2S$ is not possible if the copper active phase of a Cu based guard adsorbent designed to protect downstream catalyst is converted to Cu metal. The thermodynamic calculations have been performed by using HSC5.1 chemical equilibrium and reaction software distributed by Chempute.

Table 4 below shows that the residual level of $H_2S$ in the product will be relatively high if the copper active phase in the guard material is easily reduced to copper metal. Especially disadvantageous is the case in which copper is reduced to metal state and high sulfur capacity is desired by converting to CuS upon reaction with $H_2S$. In this case, the equilibrium concentration of $H_2S$ in the product would be higher than 10 ppm even at a temperature of 40° C.

TABLE 4

| Reaction | Temp., ° C. | Logaritm Equilibrium Constant |
|---|---|---|
| $CuO + H_2S(g) = CuS + H_2O(g)$ | 40 | 20.7 |
|  | 100 | 17.4 |
|  | 200 | 13.8 |
| $Cu_2O + H_2S(g) = Cu_2S + H_2O(g)$ | 40 | 22.3 |
|  | 100 | 18.8 |
|  | 200 | 15.2 |
| $2Cu + H_2S(g) = Cu_2S + H_2(g)$ | 40 | 8.8 |
|  | 100 | 7.2 |
|  | 200 | 5.9 |
| $Cu + H_2S(g) = CuS + H_2(g)$ | 40 | 4.6 |
|  | 100 | 2.8 |
|  | 200 | 1.9 |

Example 2

This example shows that the difficult to reduce material that was produced with the same approach as Sample 13 in Table 3 achieves very low concentrations of $H_{2S}$ even if applied at the difficult conditions of mixed phase flow which is typical for benzene saturation processes. Table 5 lists the sulfur (S) content in the effluent obtained in a test reactor with about 5 $cm^{-3}$ of the HTR sample where it was contacted first with a gas flow of hydrogen gas at 163° C. and 3103 kPa (450 psig) pressure and then in a mixed flow of a hydrocarbon blend containing about 43 mass-% n-pentane, 46% n-hexane, 7% cyclohexane, 2% heptane and 2% benzene. About 500 ppb sulfur was introduced in the feed in a form of t-butyl mercaptan.

The data shows that in all cases at the indicated hours on stream (HOS), the residual content of the product was below 40 ppb which is the detection limit of the analytical method used.

TABLE 5

| Sample | ppb S |
|---|---|
| 0.5 ppm S Feed | 500 |
| 19 HOS (Gas Phase) 1 | <40 |
| 19 HOS (Gas Phase) 2 | <40 |
| 26 HOS (Mixed Phase) 1 | <40 |
| 26 HOS (Mixed Phase) 2 | <40 |
| 43 HOS (Mixed Phase) 1 | <40 |
| 43 HOS (Mixed Phase) 2 | <40 |
| 50 HOS (Mixed Phase) 1 | <40 |
| 50 HOS (Mixed Phase) 2 | <40 |

Example 3

In a benzene saturation reactor with simulated liquid hydrocarbon feed testing a run was conducted with the difficult to reduce material as described in Example 2 at liquid feed under benzene saturation conditions. It showed sulfur capacity of the product was approximately 12 wt-%, which is consistent with the copper in the material maintaining the mostly cupric phase. This was confirmed by the subsequent X-ray analysis of the solid adsorbent which identified CuS-type crystalline compounds as the major copper phase in the solid material.

Example 4

The capability of the adsorbent used in the above examples was tested to determine its ability to adsorb sulfur at the mixed phase benzene saturation reactor inlet operating conditions with a typical testing feed. The test was done using a feed containing approximately 43% n-pentane, 46% n-hexane, 2% benzene, 7% cyclohexane, and 2% n-heptane that had been dried and the sulfur removed using high surface sodium, after which t-butyl-mercaptan was added as the sulfur species. The testing was done at 450 psig, a ratio of 0.3 H2/HC, 210-163° C., and 20 hr−1 LHSV based on the hydrocarbon feed.

A test with 0.5 ppm wt sulfur in the feed, which is the maximum allowable in a hydrotreated feed to a benzene saturation unit, showed over 90% S removal, with the product having a sulfur level below 40 ppb wt.

The invention claimed is:

1. A process for saturating benzene in a feed stream containing benzene and sulfur-compound poisons for a saturation catalyst comprising steps:
   1) sending said feed stream through a sulfur guard bed to remove said sulfur compounds from the feed stream to produce a stream containing benzene and having a reduced sulfur content, wherein said sulfur guard bed comprises sorbents comprising CuO supported on an alumina substrate and about 0.001 to 2.5% by weight of a chloride additive, wherein said sulfur sorbents are prepared by steps:
      i) mixing basic copper carbonates $CuCO_3.Cu(OH)_2$, alumina, and water to form beads,
      ii) adding NaCl or KCl to the beads of step (i);
      iii) activating the beads of step (ii) by heat treating at a temperature ranging from 280 to 500° C. to form said sorbent used for step (1); and
   2) saturating benzene in said stream containing benzene and having a reduced sulfur content of step (1) in the presence of said saturation catalyst to produce a saturation product.

2. The process of claim 1 wherein said feed stream comprises a mixed phase stream.

3. The process of claim 1 wherein said sulfur guard bed comprises about 10 to 85% by weight CuO.

4. The process of claim 1 wherein said sulfur guard bed comprises about 20 to 60% by weight CuO.

5. The process of claim 1 wherein said sulfur guard bed comprises about 30 to 50% by weight CuO.

6. The process of claim 1 wherein said sulfur guard bed further comprises a metal oxide in addition to said CuO.

7. The process of claim 1 wherein said sulfur guard bed comprises 0.3 to 1.0 weight percent of said chloride.

8. The process of claim 1 wherein said sulfur compounds are selected from the group consisting of mercaptans, sulfides, disulfides, thiophenes, carbonyl sulfide, hydrogen sulfide and mixtures thereof.

9. The process of claim 1 wherein said chloride additive provides at least a 25% reduction in water evolution during start-up of the sulfur guard bed upstream of said paraffin saturation catalyst when compared to a sulfur guard bed that does not contain said chloride additive.

10. The process of claim 1 wherein said chloride additive provides at least a 40% reduction in water evolution during start-up of the sulfur guard bed upstream of said paraffin saturation catalyst when compared to a sulfur guard bed that does not contain said chloride additive.

11. The process of claim 1 wherein a majority of said CuO is maintained in a cupric phase after exposure to make-up hydrogen at process conditions used for a hydrogen treater.

12. The process of claim 11 wherein there is no exotherm at start-up due to reduction to cuprous oxide or copper metal, since the majority of said CuO being maintained in said cupric phase.

13. The process of claim 11 wherein said CuO has an increase in capacity for adsorption as a result of said CuO being maintained in said cupric phase.

* * * * *